United States Patent [19]

Aoyama et al.

[11] Patent Number: 4,613,684
[45] Date of Patent: Sep. 23, 1986

[54] PROCESS FOR THE PREPARATION OF CARBOXYLIC ACID ESTERS

[75] Inventors: Tetsuo Aoyama; Koichi Kida; Takako Uchiyama, all of Niigata, Japan

[73] Assignee: Mitsubishi Gas Chemical Company, Inc., Tokyo, Japan

[21] Appl. No.: 655,331

[22] Filed: Sep. 27, 1984

[30] Foreign Application Priority Data

Oct. 6, 1983 [JP] Japan ................. 58-187492
Oct. 6, 1983 [JP] Japan ................. 58-187493

[51] Int. Cl.$^4$ ................. C07C 103/127; C07C 69/675
[52] U.S. Cl. ................. 560/179; 560/183; 560/206; 560/207; 560/232; 564/132
[58] Field of Search ............. 560/179, 212, 215, 232, 560/265, 183, 206, 207; 564/125, 126, 127, 128, 129, 132; 502/167, 161; 423/373; 260/465.6

[56] References Cited

U.S. PATENT DOCUMENTS

| | | | |
|---|---|---|---|
| 1,926,510 | 9/1933 | Buchanan | 560/179 |
| 2,117,600 | 5/1936 | Brill et al. | 560/232 |
| 2,356,247 | 8/1944 | Kirk et al. | 560/212 |
| 2,783,271 | 2/1957 | Eck et al. | 560/215 |
| 2,786,739 | 3/1957 | Eck et al. | 560/215 |
| 3,670,020 | 6/1972 | Moore | 564/126 |
| 3,670,021 | 6/1972 | Goetz et al. | 564/126 |
| 3,689,558 | 9/1972 | Modeen et al. | 564/128 |
| 3,980,662 | 9/1976 | Watanabe et al. | 564/127 |
| 4,055,590 | 10/1977 | Gruber et al. | 560/179 |
| 4,450,112 | 5/1984 | Wreford | 560/215 |
| 4,464,539 | 8/1984 | Hashimoto et al. | 560/212 |
| 4,539,427 | 9/1985 | Green | 564/132 |

FOREIGN PATENT DOCUMENTS

| | | | |
|---|---|---|---|
| 229321 | 4/1959 | Australia | 560/212 |
| 0040896 | 12/1981 | European Pat. Off. | 564/126 |
| 0104875 | 4/1984 | European Pat. Off. | 560/232 |
| 2454497 | 5/1976 | Fed. Rep. of Germany | 560/179 |
| 50-22533 | 7/1975 | Japan | 564/128 |
| 3015 | 1/1977 | Japan . | |
| 144524 | 12/1978 | Japan . | |
| 141216 | 12/1978 | Japan . | |
| 58-49338 | 3/1983 | Japan | 560/212 |
| 58-55444 | 4/1983 | Japan | 560/215 |

Primary Examiner—Natalie Trousof
Assistant Examiner—Bruce D. Gray
Attorney, Agent, or Firm—Frishauf, Holtz, Goodman & Woodward

[57] ABSTRACT

A commercially economical process for preparing a carboxylic acid ester from a carboxylic acid amide is disclosed. The process is very meritorious, since it produces neither ammonia nor ammonium sulfates. Rather, the process by-produces formamides which are very useful compounds as solvents. Further, formamide can easily be converted to hydrogen cyanide by dehydration. The process comprises reacting a carboxylic acid amide with a formic acid ester and/or methanol and carbon monoxide in the presence of a bicyclic amidine or tertiary amine catalyst and optionally in the co-existence of a metal carbonyl. An industrial process for preparing methyl methacrylate which is a materialization of the process shown above is described in detail referring to a figure.

19 Claims, 1 Drawing Figure

PROCESS FOR THE PREPARATION OF CARBOXYLIC ACID ESTERS

BACKGROUND OF THE INVENTION

1. Field of the Invention

The present invention relates to a process for the preparation of carboxylic acid esters which comprises reacting a carboxylic acid amide with a formic acid ester and/or an alcohol and carbon monoxide.

Carboxylic acid esters are commercially important substances, and as examples of the preparation of a carboxylic acid ester from a carboxylic acid amide, the preparation of acetic acid esters from acetamide, acrylic acid esters from acrylamide, metacrylic acid esters from methacrylamide, or α-hydroxyisobutyric acid esters from α-hydroxyisobutyramide may be cited. All these processes are commercially useful.

A preferred embodiment of the process of this invention is a process for preparing methyl methacrylate (hereinafter abbreviated as MMA) from α-hydroxyisobutyramide (hereinafter abbreviated as αHIBA) via methyl α-hydroxyisobutyrate (hereinafter abbreviated as MαHIB). This invention also relates to an industrial process for the preparation of MMA by the reaction mentioned above.

2. Description of the Prior Art

The process for the preparation of a carboxylic acid ester from a carboxylic acid amide which comprises decomposing a carboxylic acid amide with water and an alcohol in the presence of sulfuric acid is well known. However, this process has disadvantages that, for example, it gives rise to a large amount of ammonium sulfate by-product and it requires an expensive non-corrosive apparatus for the use of sulfuric acid.

In order to overcome these disadvantages, other processes which do not require the use of sulfuric acid are known for the preparation of carboxylic acid esters by the reaction between a carboxylic acid amide and an alcohol.

For example, Japanese Patent Disclosure No. 3015/1977 describes a process for the reaction of a carboxylic acid amide with a primary alcohol in the presence of a metal carboxylate which is at least partly soluble, and the carboxylate anion of which corresponds to the carboxylate residue of the desired ester. In Japanese Patent Disclosure No. 141216/1978, a process is described for the reaction of methacrylamide with a primary alcohol in the presence of a catalyst which consists of a combination of one or more species selected from copper, nickel, cobalt, and their compounds, and one or more compounds selected from a group consisting of compounds having at least one phenolic group, aldehyde group, ketone group, carboxylic acid group, amide group, or basic nitrogen containing group. In Japanese Patent Disclosure No. 144524/1978, a process is described for performing the reaction by the use of one or more catalysts selected from the group consisting of a bromide, fluoride, iodide, nitrate, phosphate, or borate of lead, cadmium, titanium, or tin.

However, all these processes cannot necessarily be regarded as commercially advantageous because they either suffers from the low activity of the catalysts, or they require an operation for the removal of ammonia from the reaction system intermittently or continuously during the reaction, in order to avoid the formation of a carboxylic acid amide and an alcohol by the reaction of a carboxylic acid ester and ammonia which are formed by the reaction.

Relative to the process for preparing MMA from αHIBA which is a preferred embodiment of the present invention, a typical process for the preparation of it known in the art is shown below.

MMA is prepared by the reaction of acetone cyanohydrin (hereinafter abbreviated as ACH) with methanol in the presence of concentrated sulfuric acid, said ACH being prepared by the reaction between hydrogen cyanide and acetone. However, this process is accompanied by the formation of a large amount of spent sulfuric acid and ammonium bisulfate by-products, and the hydrogen cyanide starting material is finally recovered as ammonium sulfate. Moreover, the quantity of ammonium sulfate which is produced, amounts to more than two tons per one ton of MMA, and this by-product formation has been a drawback of the process for the preparation of MMA by the ACH process.

SUMMARY OF THE INVENTION

We have actively worked to develop a process for preparing a carboxylic acid ester from a carboxylic acid amide which does not have the deficiencies mentioned above, and have succeeded in inventing a process which comprises reacting a carboxylic acid amide with a formic acid ester and/or an alcohol and carbon monoxide in the presence of a catalyst selected from the group consisting of bicyclic amidines and tertiary amines or a combination catalyst comprising a component selected from the group consisting of bicyclic amidines and tertiary amines and a component of metal carbonyls. The process discovered by us is a meritorious process which can easily give a desired carboxylic acid ester in high yield and high selectivity. Further, the process of this invention need not use sulfuric acid, and therefore, it is no need to use equipment made of non-corrosive materials, and it does not result in ammonium sulfate by-production. In the process of this invention, it is not necessary to remove ammonia from the reaction system and useful formamides are obtainable as a by-product. Formamides may be used, for example, as a solvent, and formamide may be recycled to the starting material for the preparation of a carboxylic acid amide because it can be converted to hydrogen cyanide by dehydration.

Further, we have succeeded to develop an excellent industrial process for the production of MMA as a materialization of the meritorious process mentioned above.

Accordingly, an object of this invention is to provide a process for preparing a carboxylic acid ester from a carboxylic acid amide, which neither needs to use sulfuric acid nor equipment made of non-corrosive materials.

Another object of this invention is to provide a process for preparing a carboxylic acid ester from a carboxylic acid amide, which does not produce an ammonium sulfate by-product.

A further object of this invention is to provide a process for preparing a carboxylic acid ester from a carboxylic acid amide, which can give industrially very useful formamides as a by-product.

A still further object of this invention is to provide an industrially useful process for preparing MMA from α-HIBA via MαHIB.

Other and more specific objects will be apparent from the following detailed description.

Thus, the gist of this invention resides in a process for the preparation of carboxylic acid esters which comprises reacting (A) a carboxylic acid amide represented by the general formula (I)

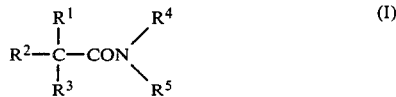

(wherein $R^1$ is selected from the group consisting of a hydrogen atom, a hydroxyl group, alkyl groups with 1 to 5 carbon atoms and alkenyl groups with 1 to 5 carbon atoms; $R^2$ and $R^3$ are independently selected from the group consisting of a hydrogen atom, alkyl groups with 1 to 5 carbon atoms and alkenyl groups with 1 to 5 carbon atoms; $R^4$ and $R^5$ are independently selected from the group consisting of a hydrogen atom and alkyl groups with 1 to 5 carbon atoms) with (B)
(i) an formic acid ester represented by the general formula (II)

(wherein $R^6$ is an alkyl group with 1 to 8 carbon atoms) and/or (ii) an alcohol represented by the general formula (III)

(wherein $R^7$ is an alkyl group with 1 to 8 carbon atoms) and carbon monoxide
in the presence of a bicyclic amidine or a tertiary amine catalyst at a temperature within a range of from 50° to 400° C.

DETAILED DESCRIPTION OF THE INVENTION

Figure 1:
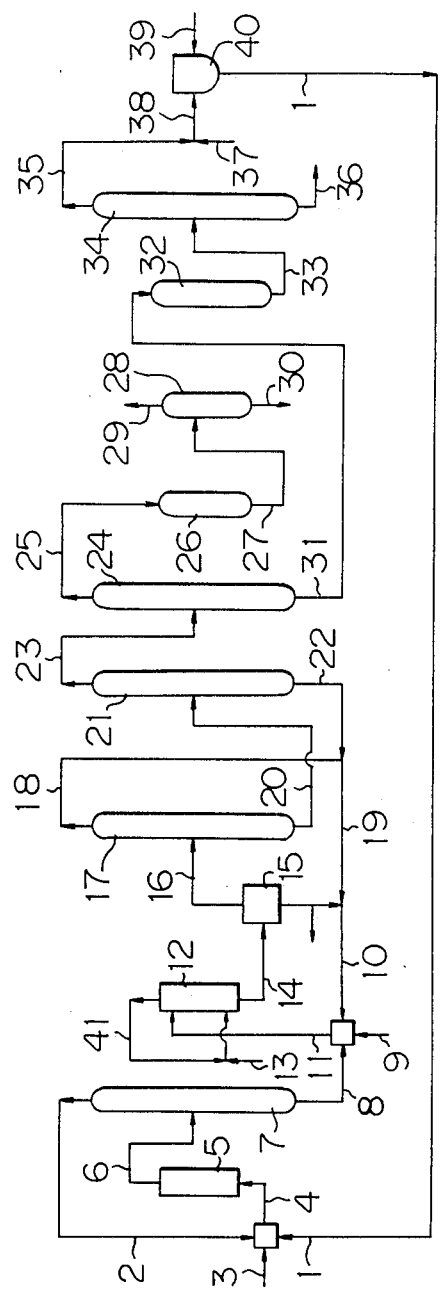
FIG. 1 is a flow diagram showing an industrial process for preparing MMA from αHIBA via MαHIB, which is a preferred embodiment of the present invention.

The carboxylic acid amide which can be used in the process of the present invention can be any conventional amide which may be prepared by the hydration of a nitrile, by the reaction of an amine and carbon monoxide, or by other reactions, and may be represented by the general formula (I) shown above.

In the formula (I), it is preferred that $R^1$ is selected from a hydrogen atom, a hydroxyl group, alkyl groups with 1 to 2 carbon atoms and alkenyl groups with 1 to 2 carbon atoms, $R^2$ and $R^3$ are independently selected from a hydrogen atom, alkyl groups with 1 to 2 carbon atoms and alkenyl groups with 1 to 2 carbon atoms, and $R^4$ and $R^5$ are independently selected from a hydrogen atom and alkyl groups with 1 to 2 carbon atoms. It is to be noted that by the term "alkenyl group" it is also intended to cover $CH_2=$group, $CH_3CH=$group and the like.

As examples of carboxylic acid amides which are represented by the formula (I), acetamide, lactamide, acrylamide, methacrylamide, and α-hydroxyisobutyramide, etc. may be cited.

The formic acid ester which is used in the present invention is represented by the general formula (II) shown above. Examples of $R^6$ in the formula (II) are alkyl group with 1 to 8 carbon atoms such as methyl, ethyl, propyl, butyl, amyl, hexyl, and octyl group etc. Methyl, ethyl, propyl or butyl group is preferable, and methyl or ethyl group is more preferable. The alcohol which may be used in the process of the present invention is represented by the general formula (III) shown above. Methyl alcohol, ethyl alcohol, propyl alcohol, butyl alcohol, amyl alcohol, hexyl alcohol, and octyl alcohol may be cited as examples of such alcohols. Methyl alcohol, ethyl alcohol, propyl alcohol or butyl alcohol is preferable, and methyl alcohol or ethyl alcohol is more preferable.

When the reaction of an alcohol and carbon monoxide with a carboxylic acid amide is carried out in the presence of a formic acid ester, the alkyl group of the alcohol should correspond to the alkyl group of the formic acid ester.

Although any secondary alkyl formate, secondary alcohol, tertiary alkyl formate, or tertiary alcohol may be used without inconvenience as the alkyl formate and the alcohol used in the present invention, it is preferred to use a primary alkyl formate or a primary alcohol in order to enhance the advantageous effect of the present invention.

As to the amount of a formic acid ester used in the present invention, the molar ratio in the reaction of a carboxylic acid amide and a formic acid ester is within the range of 1:1 to 1:15, and preferably in the range of 1:2 to 1:8. In the reaction of a carboxylic acid amide with an alcohol and carbon monoxide, the molar ratio of amide:alcohol is within the range of 1:1 to 1:30, and preferably within the range of 1:3 to 1:20. In some cases, the reaction can be performed by reacting a carboxylic acid amide with an alcohol and carbon monoxide in the presence of a formic acid ester. In this case, the ratio of a carboxylic acid amide, formic acid ester, and alcohol is within the range of 1:0.5:0.5 to 1:15:30, and preferably within the range of 1:1:2 to 1:8:15. However, these ratios are not restrictive, and other ratios may be selected depending on the kind of reactants and reaction conditions.

The catalyst used in the present invention is a bicyclic amidine or a tertiary amine, and a more preferable effect can be realized by the combined use of a bicyclic amidine or a tertiary amine with a metal carbonyl than by the use of a bicyclic amidine or a tertiary amine alone.

More specifically, 1,3-diazabicyclo[5.4.0]undecene (DBU) and 1,5-diazabicyclo[4.3.0]nonene (DBN) may be cited as examples of bicyclic amidines, and as examples of a tertiary amine used in the present invention, N-methylpyrrolidine, N-ethylpyrrolidine, 4,4'-trimethylenebis(N-methylpiperidine), N-methylpiperidine, N-ethylpiperidine, dipiperidinomethane, dipiperidinoethane, dipiperidinopropane, N,N'-dimethylpiperazine, N,N'-diethylpiperazine, trimethylamine, triethylamine, tripropylamine, tributylamine, tetramethylethylenediamine, tetramethyltetramethylenediamine, dimethylethylamine, triethylenediamine (1,4-diazabicyclo[2.2.2]octane), and N,N-dimethylcyclohexylamine may be cited.

The metal atom of a metal carbonyl used in the present invention is selected from Groups VIB, VIIB and VIII of Mendelejeff's Periodic Table of Elements.

As examples of the metal carbonyl used in the present invention, chromium carbonyl: $Cr(CO)_6$, molybdenum carbonyl: $Mo(CO)_6$, tungsten carbonyl: $W(CO)_6$, manganese carbonyl: $Mn_2(CO)_{10}$, rhenium carbonyl: $Re_2(CO)_{10}$, iron carbonyl: $Fe(CO)_5$, $Fe_2(CO)_9$, $Fe_3(CO)_{12}$, ruthenium carbonyl: $Ru_3(CO)_{12}$, osmium carbonyl: $Os_3(CO)_{12}$, cobalt carbonyl: $Co_2(CO)_8$, rhodium carbonyl: $Rh_4(CO)_{12}$, iridium carbonyl: $Ir_4(CO)_{12}$, and nickel carbonyl: $Ni(CO)_4$ may be cited.

Alternatively, instead of a metal carbonyl, any metal salt such as an oxide, hydroxide, sulfate, nitrate, carbonate, formate, acetate, oxalate, naphthenate, a chelate compound of acetylacetonate or polyaminocarboxylate, or halide of the corresponding metal, which forms the metal carbonyl under the reaction conditions, may be used in the process of the present invention.

When a bicyclic amidine or a tertiary amine is used as the catalyst in the process of the present invention, 0.001 to 1 mol of the catalyst is used per 1 mol of a carboxylic acid amide. The addition of the catalyst in excess of the required amount is uneconomical, and addition in a smaller amount results in an insufficient reaction rate, and the preferred amount is from 0.003 to 0.5 mol.

The amount of a metal carbonyl may be selected within the range of 0.0001 to 0.5 mol, preferably from 0.001 to 0.2 mol, per 1 mol of a carboxylic acid amide.

The reaction temperature of the present invention is 50°–400° C., and a temperature range of 100°–300° C. is preferred. The reaction temperature below 50° C. does not give a satisfactory result because of a low reaction rate, and a reaction temperature above 400° C. should be avoided because it will cause side reactions such as decomposition and polymerization of carboxylic acid amide, carboxylic acid ester, and formamides.

Although the reaction of a carboxylic acid amide with a formic acid ester according to the present invention may be performed under the autogenous vapor pressure of a carboxylic acid amide and a formic acid ester at the temperature of the reaction, it is preferred to operate under a pressure of carbon monoxide when other factors such as decomposition of the formic acid ester and activation of the catalyst are taken into account.

Accordingly, the reaction between a formic acid ester and a carboxylic acid amide may be performed under a carbon monoxide partial pressure of 1–500 $Kg/cm^2$, and a pressure of 1–400 $Kg/cm^2$ is preferred, and a pressure of 20–400 $Kg/cm^2$ is more preferred because the use of an excessively high pressure is not practical. In the reaction of a carboxylic acid amide with an alcohol and carbon monoxide, the carbon monoxide partial pressure is 10–500 $Kg/cm^2$, and a partial pressure of 20–400 $Kg/cm^2$ is preferred, and a partial pressure of 30–400 $Kg/cm^2$ is more preferred.

In the present invention, it is not necessary to use a solvent, but acetone, ethylether, methyl formate or dimethyl formamide, etc. may be used as the solvent.

The present invention may be operated by a batch, a semi-batch, or a continuous process.

The process of the present invention has an enormous commercial value because the present invention not only allows the production of a carboxylic acid ester without the formation of ammonia as a by-product by the reaction of a carboxylic acid amide with a formic acid ester, or by the reaction of a carboxylic acid amide with an alcohol and carbon monoxide, but also it simultaneously produces formamides which are useful as solvents and formamide can easily be converted to hydrogen cyanide by dehydration and hydrogen cyanide thus obtained may be recycled as a starting material.

A preferred embodiment of the present invention is a process for preparing methyl methacrylate (MMA) from α-hydroxyisobutyramide (αHIBA) via methyl α-hydroxyisobutyrate (MαHIB). Accordingly, in the following, an industrial process for preparing MMA which is a materialization of the process of this invention is explained.

This process is a kind of acetone cyanohydrin (ACH) process, and this process can remove the deficiencies aforementioned relative to known processes for preparing MMA. In this process, the hydrogen cyanide is recovered unchanged as hydrogen cyanide without the formation of ammonium sulfate by-product. This process comprises the steps of producing αHIBA by hydration of ACH which is formed by the reaction of hydrogen cyanide with acetone, converting said αHIBA into MαHIB and formamide by the reaction with carbon monoxide and methanol, separating MαHIB and formamide, dehydrating MαHIB to give MMA, dehydrating formamide to hydrogen cyanide, and recycling hydrogen cyanide thus obtained to the reaction with acetone.

In the process of the present invention, the preparation of ACH by the reaction between hydrogen cyanide and acetone may be performed by a process which is widely known to the art. Thus, hydrogen cyanide and acetone are mixed in the liquid phase under atmospheric pressure, and the reaction is performed with cooling and stirring in the presence of a small amount of an alkali or an amine catalyst. The reaction proceeds quantitatively, and ACH is obtained in a high yield.

The next step which is the hydration reaction of ACH, may be performed in the vapor phase or the liquid phase, but the liquid phase is preferable. When this reaction is performed in the liquid phase, the reaction may be performed in the presence of a strong acid such as sulfuric acid. However, as it is difficult to separate the acid economically, it is preferred to react ACH with water in a solvent in the presence of a metal catalyst or an alkali catalyst.

Copper, copper oxide, nickel, manganese oxide, etc. may be generally used as the metal catalyst, and manganese oxide is especially preferred. The use of a solvent is effective in carrying out this reaction. A hydrophilic solvent such as acetone and methanol is suitable, and acetone is especially preferred. The reaction may be operated by either a batch or a continuous process, but the use of a continuous apparatus equipped with a fixed catalyst bed is commercially suitable. The reaction may proceed under atmospheric pressure or above, at a reaction temperature of 20°–200° C. It is also possible to produce αHIBA by microbial or enzymatic hydration.

The αHIBA thus produced is converted to MαHIBA by the reaction with methanol and carbon monoxide. With respect to carbon monoxide used in the process of the present invention, although various gas mixtures which contain carbon monoxide may be used, the reaction proceeds faster with a higher efficiency as the purity of the gas is increased. Conventional commercial methanol is sufficient as the methanol used in the present invention. Relative to the reaction of αHIBA with methanol and carbon monoxide, the reaction conditions such as type of catalyst, amount of catalyst, reaction temperature, reaction pressure, molar ratio of reactants, etc. are aforementioned.

MαHIB thus obtained is separated from formamide by distillation under a reduced pressure, and is converted then to MMA by dehydration. Although sulfuric acid may be used as the dehydration agent, its use is not preferred because its use causes trouble during the separation step. The dehydration may also be realized by the use of acetic anhydride, calcium oxide, etc. Commercially, it is suitable to conduct the dehydration reaction either in the liquid phase by distilling out MMA or water in the presence of a strong acid catalyst such as sulfuric acid, or in a vapor phase by passing through a solid catalyst. The latter process is especially preferred. In the vapor phase, fixed bed process, a solid acid catalyst exemplified by silica-alumina is generally used. The presence of steam or an inert gas is effective in reducing the deposition of carbonaceous products onto the catalyst. The reaction at 200°–550° C. under atmospheric pressure is appropriate for the reaction by the vapor phase, fixed bed process.

The formamide which is separated from MαHIB is converted to hydrogen cyanide by dehydration. This dehydration reaction is conducted by passing formamide through a solid catalyst at a temperature of 200°–800° C. The reaction is conducted in the vapor phase and the design of the reactor may be either a fixed bed or a fluidized bed. Alumina type, iron-silica type, manganese-copper type catalyst and the like are used with satisfactory results. The yield of the reaction is high, and almost quantitative yields of hydrogen cyanide and water are formed.

Hydrogen cyanide is separated from water, and hydrogen cyanide is recycled to the ACH preparation step which is described hereinbefore.

DESCRIPTION OF THE PREFERRED EMBODIMENTS

A preferred embodiment of an industrial process for preparing MMA mentioned above is explained referring to FIG. 1.

This embodiment was carried out by using flow-sheet shown in FIG. 1. ACH at a rate of 851 g/hr which was charged from the ACH process through line 1, 580 g/hr of acetone and 360 g/hr of water through recovery line 2, and 180 g/hr of water through line 3 were mixed, and the mixture was charged through line 4 to a hydration apparatus 5 in which 1 liter of manganese oxide catalyst is packed as a fixed bed. The reaction was operated under pressure so that the reactants remain as a liquid phase at a reaction temperature of 60° C. The hydration product which was withdrawn through line 6 at a rate of 1970 g/hr contained 47.6 wt% of αHIBA, 29.5 wt% of acetone, and 18.3 wt% of water. The reaction products were charged to a low-boiling point material splitter 7, and acetone and water were recovered from the overhead and were recycled to the starting material system, and crude αHIBA was withdrawn through line 8 from the column bottom. The bottom liquid is admixed with 300 g/hr of methanol through line 9, 980 g/hr of unreacted αHIBA through line 10, 2681 g/hr of unreacted methanol and 40 g/hr and 80 g/hr respectively of $Cr(CO)_6$ and N-methylpyrrolidine catalysts, and the mixture was charged to a tubular reactor 12 through line 11, and was allowed to contact carbon monoxide through line 13 under a pressure of 200 $Kg/cm^2G$ at a temperature of 180° C. The CO is absorbed at a rate of 260 g/hr and unreacted carbon monoxide was discharged from the top of the reactor to line 41 and was recycled to line 13. In the start-up operation, the charge rate of fresh methanol was 1600 g/hr, but when the operation reached normal run conditions, the charge rate of fresh methanol was reduced to 300 g/hr. In the reactor 12, 5337 g/hr of the esterified product was obtained. It contained 18.2 wt% of MαHIB, 6.9 wt% of formamide, 19.3 wt% of unreacted αHIBA, and 50.0 wt% of methanol.

The liquid product was charged to a film evaporator 15 through line 14, in which the catalysts and a small amount of high boiling components were removed. Most of the catalysts and high boiling componenets were recycled to line 10 while a small part were purged. The distilled fraction was charged to a methanol recovery column 17 through line 16, where unreacted methanol and low-boiling by-products were separated and recovered from the overhead, and recycled to line 10 via lines 18 and 19. The mixture containing formamide, MαHIB, and unreacted αHIBA which was recovered from the column bottom, was sent to an αHIBA separation column 21 through line 20, and 980 g/hr of unreacted αHIBA was withdrawn through line 22 and was recycled to line 10 via lines 22 and 19. The distillate obtained from the overhead was sent to a formamide separation column 24 through line 23, and MαHIB and formamide were obtained from the column top and the column bottom respectively. The overhead at a rate of 1030 g/hr was charged through line 25 to a MαHIB dehydration apparatus 26 and the dehydration reaction was conducted with a fixed bed silica-alumina catalyst in a vapor phase at 500° C. The dehydration products containing MMA and water were charged through line 27 to a decanter 28, where the water is separated, and 850 g/hr of crude MMA which constitutes the upper layer was withdrawn through line 29 and was sent to a purification process (not shown in the figure). Water was withdrawn through line 30. The formamide which is withdrawn at a rate of 360 g/hr from the column bottom of 24 was sent through line 31 to a formamide dehydration reactor 32, where it was submitted to a vapor phase dehydration process at 550° C. in the presence of an iron oxide-alumina catalyst. The reaction product was charged to a hydrogen cyanide recovery column 34 through line 33. From the column top, 212 g/hr of HCN was recovered through line 35, and water was withdrawn from the column bottom through line 36. Fresh HCN was added through line 37 at a rate of 64 g/hr, and the combined HCN was charged through line 38 to an acetone cyanohydrin synthesis apparatus 40, to which 593 g/hr of acetone and a catalyst (sodium hydroxide) were charged through line 38, and 851 g/hr of ACH thus formed is recycled as the starting material through line 1.

This process has an enormous commercial value because the process of the present invention allows recycled use of the hydrogen cyanide starting material via formamide during the process of the preparation of MMA, without the formation of an ammonia by-product.

In the following examples, reactions for preparing a carboxylic acid ester from a carboxylic acid amide are shown, however, these examples are shown for illustration purpose only, and should not be construed to restricting the present invention.

Incidentally, in the examples, unless the contrary is stated, the conversion is calculated in mole % based on the carboxylic acid amide which is used and the yields of the carboxylic acid ester and formamide are calculated in mole % based on the carboxylic acid amide which is used and the selectivities to the carboxylic acid ester and formamide are calculated in mole % by the autoclave as described in Example 1 are shown in Table 1.

TABLE 1

| | Example No. | | | | | | |
|---|---|---|---|---|---|---|---|
| | 2 | 3 | 4 | 5 | 6 | 7 | 8 |
| αHIBA*[1] mmol | 70 | 70 | 70 | 70 | 70 | 70 | 70 |
| methanol mmol | 560 | 560 | 560 | 560 | 560 | 560 | 560 |
| tertiary amine or amidine | | | | | | | |
| compound | TEDA*[2] | NMPR*[3] | DBN*[4] | DBU*[5] | NMPP*[6] | NMPP | NMPR |
| mmol | 5 | 8 | 5 | 3 | 8 | 8 | 8 |
| metal carbonyl | | | | | | | |
| compound | — | — | — | — | — | $Cr(CO)_6$ | $Cr(CO)_6$ |
| mmol | — | — | — | — | — | 1.8 | 1.8 |
| reaction pressure $Kg/cm^2$ | 200 | 200 | 200 | 200 | 200 | 200 | 200 |
| reaction temperature °C. | 180 | 180 | 180 | 200 | 180 | 180 | 180 |
| reaction time min | 120 | 120 | 120 | 180 | 120 | 120 | 40 |
| αHIBA conversion % | 41.0 | 28.5 | 42.9 | 51.0 | 26.3 | 58.9 | 52.1 |
| **MαHIB*[7]** | | | | | | | |
| yield mol % | 40.3 | 28.2 | 42.1 | 49.7 | 26.2 | 56.2 | 50.3 |
| selectivity % | 98.4 | 98.9 | 98.1 | 97.5 | 99.5 | 95.4 | 96.5 |
| formamide | | | | | | | |
| yield mol % | 37.6 | 26.2 | 37.8 | 45.2 | 23.4 | 49.5 | 46.6 |
| selectivity % | 91.6 | 92.0 | 88.1 | 88.6 | 89.0 | 84.0 | 89.5 |

| | Example No. | | | | | | |
|---|---|---|---|---|---|---|---|
| | 9 | 10 | 11 | 12 | 13 | 14 | 15 |
| αHIBA*[1] mmol | 70 | 70 | 70 | 70 | 70 | 70 | 70 |
| methanol mmol | 560 | 560 | 560 | 600 | 550 | 560 | 560 |
| tertiary amine or amidine | | | | | | | |
| compound | NMPR*[3] | NMPP*[6] | NMPR | NMPR | NMPR | TBA*[8] | TEDA*[2] |
| mmol | 8 | 4 | 8 | 8 | 8 | 10 | 5 |
| metal carbonyl | | | | | | | |
| compound | $Fe(CO)_5$ | $RuO_2$ | $Mo(CO)_6$ | $W(CO)_6$ | $Re_2(CO)_{10}$ | $Cr(CO)_6$ | $Cr(CO)_8$ |
| mmol | 2.0 | 1.5 | 1.9 | 1.7 | 0.8 | 1.8 | 1.8 |
| reaction pressure $Kg/cm^2$ | 200 | 200 | 200 | 200 | 200 | 200 | 200 |
| reaction temperature °C. | 180 | 180 | 180 | 180 | 180 | 180 | 180 |
| reaction time min | 120 | 120 | 60 | 60 | 120 | 120 | 120 |
| αHIBA conversion % | 50.8 | 54.8 | 52.7 | 48.0 | 47.5 | 45.9 | 50.7 |
| **MαHIB*[7]** | | | | | | | |
| yield mol % | 49.3 | 53.3 | 50.5 | 46.7 | 45.6 | 45.0 | 49.6 |
| selectivity % | 97.1 | 97.3 | 95.8 | 97.3 | 96.1 | 98.0 | 97.9 |
| formamide | | | | | | | |
| yield mol % | 87.7 | 43.2 | 45.6 | 42.7 | 41.6 | 41.6 | 44.6 |
| selectivity % | 90.3 | 81.0 | 86.6 | 89.0 | 87.6 | 90.7 | 88.0 |

*[1] α-hydroxyisobutyramide;
*[2] triethylenediamine;
*[3] N—methylpyrrolidine;
*[4] 1,5-diazabicyclo[4.3.0]nonene;
*[5] 1,3-diazabicyclo[5.4.0]undecene;
*[6] N—methylpiperidine;
*[7] methyl-α-hydroxyisobutyrate;
*[8] tri-n-butylamine formula: yield × 100/the conversion.

EXAMPLE 1

Into a 100 ml stainless autoclave were charged 70 mmol of αHIBA and 560 mmol of methanol with 3.0 mmol of DBU as the catalyst. The autoclave was purged and pressurized by carbon monoxide, and was heated and agitated. When the inner temperature of autoclave reached to 180° C., the reaction was continued for 180 min. by supplying carbon monoxide so as to keep the pressure at 150 $Kg/cm^2$.

After cooling, the pressure of autoclave was reduced to atmospheric pressure, the reaction products were taken out, and analyzed by gas-chromatography.

The conversion of αHIBA was 45.0%, the yield of MαHIB was 44.4%, and the selectivity was 98.6%. The yield of formamide was 40.8% with a selectivity of 90.8%.

EXAMPLES 2-15

The results of the reactions performed by the same experimental procedure and by the use of the same

EXAMPLE 16

The reaction was conducted by the same procedure in the same autoclave as Example 1, except that 70 mmol of lactamide and 560 mmol of methanol were used, with 3.0 mmol of DBU as the catalyst.

The conversion rate of lactamide was 55.5%, the yield of methyl lactate was 45.5%, and the selectivity was 82.0%. The yield of formamide by this reaction was 45.0% with the selectivity of 81.1%.

EXAMPLE 17

The reaction was conducted by the same procedure in the same autoclave as Example 1, except that 70 mmol of methacrylamide and 560 mmol of methanol were used with 3.0 mmol of DBU as the catalyst.

The conversion of methacrylamide was 39.5%, the yield of methyl methacrylate was 34.6%, and the selectivity was 87.6%. The yield of formamide by this reaction was 35.1% with the selectivity of 88.9%.

EXAMPLE 18

Into the same autoclave used in Example 1, 70 mmol of αHIBA, 350 mmol of methyl formate and 5 mmol of DBU as the catalyst were charged. After the autoclave was purged with nitrogen, the autoclave was heated and agitated. After the reaction was continued for 180 min. under the autogeneous pressure at 180° C., the autoclave was cooled and the pressure thereof was reduced to atmospheric pressure. And then the reaction products were taken out and analyzed by gas-chromatography. As the result, the conversion of αHIBA was 53.0%, the yield of MαHIB was 37.4% and the selectivity to the MαHIB was 70.6%. The yield of formamide was 25.8% and the selectivity thereto was 48.7%.

EXAMPLE 19

Into the same autoclave used in Example 1, 70 mmol of αHIBA, 350 mmol of methyl formate and 5 mmol of DBU as the catalyst were charged. After the autoclave was purged with carbon monoxide gas, carbon monoxide gas was further added until the autoclave pressure reached to 50 Kg/cm$^2$, and then the autoclave was heated and agitated. After the reaction was continued for 180 min. at 180° C., the autoclave was cooled and the pressure of autoclave was reduced to atmospheric pressure. Then the reaction products were taken out and analyzed by gas-chromatography. The conversion of αHIBA was 51.9%, the yield of MαHIB was 40.6% and the selectivity thereto was 78.2%. The yield of formamide was 31.9% and the selectivity thereto was 61.5%.

EXAMPLE 20

An experiment was conducted in the same manner as in Example 19, except that 70 mmol of αHIBA, 175 mmol of methyl formate and 5 mmol of DBU as the catalyst were charged into the same autoclave used in Example 1. As the result, the conversion of αHIBA was 45.9%, the yield of MαHIB was 34.9% and the selectivity thereto was 76.1%. The yield of formamide was 27.6% and the selectivity thereto was 60.1%.

EXAMPLE 21

An experiment was conducted in the same manner as in Example 19, except that 70 mmol of αHIBA, 350 mmol of methyl formate and 5 mmol of DBU as the catalyst were charged into the same autoclave used in Example 1 and the reaction temperature of 150° C. and reaction time of 300 min. were used.

As the result, the conversion of αHIBA was 50.7%, the yield of MαHIB was 45.9% and the selectivity thereto was 90.5%. The yield of formamide was 39.6% and the selectivity thereto was 78.2%.

EXAMPLE 22

Into the same autoclave used in Example 1, 70 mmol of αHIBA, 560 mmol of methanol, 56 mmol of methyl formate and 1.8 mmol of Cr(CO)$_6$ and 8 mmol of N-methylpirrolidine as the catalysts were charged. The autoclave was purged with carbon monoxide gas and was further pressurized with carbon monoxide gas and the autoclave was heated with shaking. When inner temperature of the autoclave was reached to 180° C., the reaction was conducted for 25 min. by supplying carbon monoxide gas so as to maintain the reaction pressure of 200 Kg/cm$^2$. After cooling, the autoclave pressure was reduced to an atmospheric pressure, and then the reaction products were taken out and analyzed by gas-chromatography.

The conversion of αHIBA was 60.8%, the yield of MαHIB was 57.0% and the selectivity thereto was 93.7%. The yield of the formamide was 49.4% and the selectivity thereto was 81.3%.

We claim:

1. A process for the preparation of a carboxylic acid ester of the formula

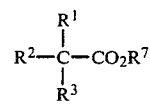

and an amide of the formula

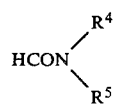

which comprises reacting (A) a carboxylic acid amide represented by the formula

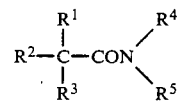

with (B) an alcohol of the formula R$^7$OH and carbon monoxide in the presence of (i) a bicyclic amidine or a tertiary amine catalyst or (ii) a bicyclic amidine or a tertiary amine catalyst together with a metal carbonyl catalyst in which the metal is selected from Groups VIB, VIIB and VIII of Mendelejeff's Periodic Table of Elements, at a temperature of from 50° to 400° C. under a carbon monoxide partial pressure of from 10 to 500 Kg/cm$^2$, the molar ratio of said alcohol/said carboxylic acid amide being in the range of from 1 to 30, wherein R$^1$ is selected from the group consisting of a hydrogen atom, a hydroxyl group, alkyl groups with 1 to 5 carbon atoms and alkenyl groups with 1 to 5 carbon atoms; R$^2$ and R$^3$ are independently selected from the group consisting of a hydrogen atom, alkyl groups with 1 to 5 carbon atoms and alkenyl groups with 1 to 5 carbon atoms; R$^4$ and R$^5$ are independently selected from the group consisting of a hydrogen atom and alkyl groups with 1 to 5 carbon atoms; and R$^7$ is an alkyl group with 1 to 8 carbon atoms.

2. The process of claim 1, wherein said temperature is from 100° to 300° C.

3. The process of claim 1, wherein the amount of said amidine or said tertiary amine is from 0.001 to 1 mole per 1 mole of said carboxylic acid amide.

4. The process of claim 1, wherein the amount of said alcohol is from 3 to 20 moles per 1 mole of said carboxylic acid amide and the reaction is conducted under a carbon monoxide partial pressure of from 20 to 400 Kg/cm$^2$.

5. The process of claim 3, wherein the amount of said metal carbonyl is from 0.0001 to 0.5 mole per 1 mole of said carboxylic acid amide.

6. The process of claim 3, wherein said carboxylic acid amide is α-hydroxyisobutyramide and said alcohol is methanol.

7. The process of claim 6, wherein the amount of said metal carbonyl is from 0.0001 to 0.5 mole per 1 mole of said α-hydroxyisobutyramide.

8. The process of claim 1, wherein said carboxylic acid amide and said alcohol and carbon monoxide are reacted in the presence of a bicyclic amidine or a tertiary amine catalyst together with a metal carbonyl catalyst and said metal is selected from the group consisting of Cr, Mo, W, Mn, Re, Fe, Ru, Os, Co, Rh, Ir and Ni.

9. A process for the preparation of methyl methacrylate and formamide which comprises reacting α-hydroxyisobutyramide with methanol and carbon monoxide at a temperature of from 50° to 400° C. under a carbon monoxide partial pressure of from 10 to 500 Kg/cm² in the presence of (i) a bicyclic amidine or a tertiary amine catalyst or (ii) a bicyclic amidine or a tertiary amine catalyst together with a metal carbonyl catalyst in which the metal is selected from Groups VIB, VIIB and VIII of Mendelejeff's Periodic Table of Elements to form methyl α-hydroxyisobutyrate and formamide, wherein the amount of said amidine or said tertiary amine is from 0.001 to 1 mole per 1 mole of said α-hydroxyisobutyramide, and when said catalyst also contains said metal carbonyl the amount of said metal carbonyl is from 0.0001 to 0.5 mole per 1 mole of said α-hydroxyisobutyramide and the amount of said methanol is from 1 to 30 moles per 1 mole of said α-hydroxyisobutyramide; separating said methyl α-hydroxyisobutyrate and formamide from each other; and dehydrating said methyl α-hydroxyisobutyrate to form methyl methacrylate.

10. A process for the preparation of methyl α-hydroxyisobutyrate which comprises preparing acetone cyanohydrin by reacting acetone and hydrogen cyanide; hydrating said acetone cyanohydrin to form α-hydroxyisobutyramide; reacting said α-hydroxyisobutyramide with methanol and carbon monoxide at a temperature of from 50° to 400° C. under a carbon monoxide partial pressure of from 10 to 500 Kg/cm² in the presence of (i) a bicyclic amidine or a tertiary amine catalyst or (ii) a bicyclic amidine or a tertiary amine catalyst together with a metal carbonyl catalyst in which the metal is selected from Groups VIB, VIIB and VIII of Mendelejeff's Periodic Table of Elements to form methyl α-hydroxyisobutyrate and formamide, wherein the amount of said amidine or said tertiary amine is from 0.001 to 1 mole per 1 mole of said α-hydroxyisobutyramide, and when said catalyst also contains said metal carbonyl, the amount of said metal carbonyl is from 0.0001 to 0.5 mole per 1 mole of said α-hydroxyisobutyramide and the amount of said methanol is from 1 to 30 moles per 1 mole of said α-hydroxyisobutyramide; separating said methyl α-hydroxyisobutyrate and formamide from each other; dehydrating said formamide to form hydrogen cyanide and recycling said hydrogen cyanide to said first mentioned acetone cyanohydrin preparation step.

11. The process of claim 10, wherein said dehydration of formamide is conducted in the vapor phase at a temperature of from 200° to 800° C. in the presence of a metal or metal oxide catalyst.

12. The process of claim 10, wherein said reaction of acetone and hydrogen cyanide is an addition reaction conducted in the liquid phase under cooling in the presence of a basic catalyst.

13. The process of claim 10, wherein said hydration of acetone cyanohydrin is conducted by reacting acetone cyanohydrin with water in liquid phase at a temperature of from 20° to 200° C. in the presence of a metal or metal oxide catalyst and in the presence of a hydrophilic solvent.

14. The process as claimed in claim 10, wherein the reaction for producing methyl α-hydroxyisobutyrate from α-hydroxyisobutyramide is conducted in the presence of an organic solvent.

15. The process as claimed in claim 11, wherein the reaction of acetone and hydrogen cyanide is conducted in liquid phase under cooling in the presence of a basic catalyst; and the hydration of acetone cyanohydrin is conducted in liquid phase at a temperature of from 20° to 200° C. by using a metal or metal oxide catalyst in the presence of a hydrophilic solvent.

16. The process of claim 10, wherein said carboxylic acid amide and said alcohol and carbon monoxide are reacted in the presence of a bicyclic amidine or a tertiary amine catalyst together with a metal carbonyl catalyst and said metal is selected from the group consisting of Cr, Mo, W, Mn, Re, Fe, Ru, Os, Co, Rh, Ir and Ni.

17. A process for the preparation of methyl methacylate which comprises preparing acetone cyanohydrin by reacting acetone and hydrogen cyanide; hydrating said acetone cyanohydrin to form α-hydroxyisobutyramide; reacting said α-hydroxyisobutyramide with methanol and carbon monoxide at a temperature of from 50° to 400° C. under a carbon monoxide partial pressure of from 10 to 500 Kg/cm² in the presence of (i) a bicyclic amidine or a tertiary amine catalyst or (ii) a bicyclic amidine or a tertiary amine catalyst together with a metal carbonyl catalyst in which the metal is selected from Groups VIB, VIIB and VIII of Mendelejeff's Periodic Table of Elements to form methyl α-hydroxyisobutyrate and formamide, wherein the amount of said amidine or said tertiary amine is from 0.001 to 1 mole per 1 mole of said α-hydroxyisobutyramide, and when said catalyst also contains said metal carbonyl, the amount of said metal carbonyl is from 0.0001 to 0.5 mole per 1 mole of said α-hydroxyisobutyramide and the amount of said methanol is from 1 to 30 moles per 1 mole of said α-hydroxyisobutyramide; separating said methyl α-hydroxyisobutyrate and formamide from each other; dehydrating said methyl α-hydroxyisobutyrate to form methyl methyacrylate; dehydrating said formamide to form hydrogen cyanide and recycling said hydrogen cyanide to said first mentioned acetone cyanohydrin preparation step.

18. The process of claim 17, wherein the reaction of acetone and hydrogen cyanide is conducted in liquid phase under cooling in the presence of a basic catalyst; the hydration of acetone cyanohydrin is conducted in liquid phase at a temperature of from 20° to 200° C. by using a metal or metal oxide catalyst in the presence of a hydrophilic solvent; the dehydration of methyl α-hydroxyisobutyrate is conducted in vapor phase at a temperature of from 200° to 550° C. in the presence of a solid acid catalyst; and the dehydration of formamide is conducted in vapor phase at a temperature of from 200° to 800° C. by the use of a metal or metal oxide catalyst.

19. The process of claim 18, wherein said carboxylic acid amide and said alcohol and carbon monoxide are reacted in the presence of a bicyclic amidine or a tertiary amine catalyst together with a metal carbonyl catalyst and said metal is selected from the group consisting of Cr, Mo, W, Mn, Re, Fe, Ru, Os, Co, Rh, Ir and Ni.

* * * * *